United States Patent
Schwartz

(10) Patent No.: US 8,315,696 B2
(45) Date of Patent: Nov. 20, 2012

(54) IDENTIFYING CRITICAL CFAE SITES USING CONTACT MEASUREMENT

(75) Inventor: Yitzhack Schwartz, Haifa (IL)

(73) Assignee: Biosense Webster (Israel), Ltd. (IL)

( * ) Notice: Subject to any disclaimer, the term of this patent is extended or adjusted under 35 U.S.C. 154(b) by 0 days.

(21) Appl. No.: 12/963,818

(22) Filed: Dec. 9, 2010

(65) Prior Publication Data

US 2012/0150021 A1    Jun. 14, 2012

(51) Int. Cl.
*A61B 5/0402* (2006.01)
(52) U.S. Cl. ........................... 600/513; 600/509
(58) Field of Classification Search .................. 600/513, 600/509
See application file for complete search history.

(56) References Cited

U.S. PATENT DOCUMENTS

| | | | |
|---|---|---|---|
| 6,298,257 B1 | 10/2001 | Hall | |
| 2007/0197929 A1 | 8/2007 | Porath et al. | |
| 2009/0076476 A1* | 3/2009 | Barbagli et al. | 604/500 |
| 2009/0093806 A1 | 4/2009 | Govari et al. | |
| 2009/0138007 A1 | 5/2009 | Govari et al. | |
| 2010/0168557 A1 | 7/2010 | Deno | |

OTHER PUBLICATIONS

Chugh, A. *Deconstructing CFAEs: Just How Complex and Fragmented Are They?* Heart Rhythm (2009), doi:10.1016/j.hrthm.2010.11.021.
Kirchhof, P. et al. *Recording Monophasic Action Potentials*. Practical Methods in Cardiovascular Research (2005, Part 2 &3, 417-431.
Kong, M.H. et al. *Efficacy of adjunctive ablation of complex fractionated atrial electrograms and pulmonary vein isolation for the treatment of atrial fibrillation: a meta-analysis of randomized controlled trials*. Europace (2010), doi:10.1093, 1-12.
Narayan, S.M. et al. *Classifying Fractionated Electrograms in Human Atrial Fibrillation Using Monophasic Action Potentials and Activation Mapping: Evidence for Localized Drivers, Rate Acceleration and Non-Local Signal Etiologies*. Heart Rhythm (2010), doi:10.1016/jhrthm.2010.10.020.
U.S. Appl. No. 12/633,324, filed Dec. 8, 2009—pending.
European Search Report Appln No. 11192651.5-1265 dated Mar. 19, 2012.

* cited by examiner

*Primary Examiner* — Eric D. Bertram
(74) *Attorney, Agent, or Firm* — William A. Schoneman

(57) ABSTRACT

A method for mapping includes receiving electrical inputs measured by a probe at respective locations in a chamber of a heart of a subject. The electrical inputs are processed to identify complex fractionated electrograms. At each of the respective locations, a respective contact quality between the probe and a tissue in the chamber is measured. A map of the complex fractionated electrograms in the chamber is created using the electrical inputs and the measured contact quality.

23 Claims, 4 Drawing Sheets

IDENTIFYING CRITICAL CFAE SITES USING CONTACT MEASUREMENT

FIELD OF THE INVENTION

The present invention relates generally to diagnosis and treatment of cardiac arrhythmias, and specifically to methods and apparatus for identification of arrhythmogenic sites within the heart.

BACKGROUND OF THE INVENTION

Over the past decade, mapping studies in human atrial fibrillation (AF) have found that atrial electrograms during sustained atrial fibrillation have three distinct patterns: single potential, double potential and complex fractionated atrial electrograms (CFAE). Areas of CFAE tend to be atrial fibrillation substrate sites and become important target sites for treatment, typically by ablation of endocardial tissue. For this reason, some practitioners now treat left atrial fibrillation not only by the accepted practice of ablating tissue around the ostia of the pulmonary veins (known as pulmonary vein isolation, or PVI), but also by ablating areas having persistent CFAEs.

U.S. Patent Application Publication 2007/0197929, whose disclosure is incorporated herein by reference, describes automatic detection and mapping of CFAEs within cardiac chambers. Electrogram signals are analyzed to count the number of complexes whose amplitude and peak-to-peak intervals meet certain criteria. Functional maps indicating average complex interval, shortest complex interval, and confidence levels are produced for display.

Kong et al. describe a meta-analysis of six randomized controlled trials to compare PVI alone with PVI plus CFAE ablation, in "Efficacy of Adjunctive Ablation of Complex Fractionated Atrial Electrograms and Pulmonary Vein Isolation for the Treatment of Atrial Fibrillation: A Meta-Analysis of Randomized Controlled Trials," *Europace* (2010), which is incorporated herein by reference. The authors found PVI followed by adjunctive CFAE ablation to be associated with increased freedom from AF after a single procedure. On the other hand, adjunctive CFAE ablation increased procedural, fluoroscopy, and radio frequency (RF) application times. The authors concluded that the risk/benefit profile of adjunctive CFAE ablation deserves additional study and longer-term follow-up.

When a catheter is inserted into a chamber of the heart and brought into contact with the inner heart wall, it is generally important that the distal tip of the catheter engage the endocardium with sufficient pressure to ensure good contact. Excessive pressure, however, may cause undesired damage to the heart tissue and even perforation of the heart wall. A number of patent publications describe catheters with integrated pressure sensors for sensing tissue contact. For example, U.S. Patent Application Publications 2009/0093806 and 2009/0138007, whose disclosures are incorporated herein by reference, describe catheters with this sort of pressure sensing.

SUMMARY OF THE INVENTION

Embodiments of the present invention that are described hereinbelow provide improved methods and systems for reliable mapping of fractionated electrograms.

There is therefore provided, in accordance with an embodiment of the present invention, a method for mapping, which includes receiving electrical inputs measured by a probe at respective locations in a chamber of a heart of a subject. The electrical inputs are processed to identify complex fractionated electrograms. At each of the respective locations, a respective contact quality between the probe and a tissue in the chamber is measured. A map of the complex fractionated electrograms in the chamber is created using the electrical inputs and the measured contact quality.

In some embodiments, measuring the respective contact quality includes assessing an angle of contact between the probe and the tissue and may include measuring the respective contact quality further includes measuring a force of contact between the probe and the tissue. Typically, creating the map includes rejecting the inputs for which the angle of contact is outside a predetermined angular range of a perpendicular to the tissue. The angle of contact may be assessed by measuring a bend angle of a distal end of the probe. Additionally or alternatively, creating the map may include rejecting the inputs for which the force of contact is outside a predetermined range.

In one embodiment, the chamber is a left atrium of the heart, and the method includes ablating sites in the left atrium at which the complex fractionated electrograms were detected while the contact quality satisfied a predetermined contact criterion. The predetermined contact criterion typically requires that a force of contact and an angle of contact between the probe and the tissue be within respective predetermined ranges.

In a disclosed embodiment, creating the map includes selectively mapping active sites of fractionated electrical activity responsively to the measured contact quality.

There is also provided, in accordance with an embodiment of the present invention, mapping apparatus, including a probe, which is configured to sense electrical activity in a chamber of a heart of a subject. A processor is configured to receive and process electrical inputs from the probe at multiple locations in the chamber so as to identify complex fractionated electrograms, to measure, at each of the locations, a respective contact quality between the probe and a tissue in the chamber, and to create a map of the complex fractionated electrograms in the chamber using the electrical inputs and the measured contact quality.

There is additionally provided, in accordance with an embodiment of the present invention, a computer software product, including a computer-readable medium in which program instructions are stored, which instructions, when read by a processor, cause the processor to receive electrical inputs from a probe in response to electrical activity at multiple locations in a chamber of a heart of a subject, to process the electrical inputs so as to identify complex fractionated electrograms, to measure, at each of the locations, a respective contact quality between the probe and a tissue in the chamber, and to create a map of the complex fractionated electrograms in the chamber using the electrical inputs and the measured contact quality.

The present invention will be more fully understood from the following detailed description of the embodiments thereof, taken together with the drawings in which:

DETAILED DESCRIPTION OF EMBODIMENTS

Overview

Figure 1:
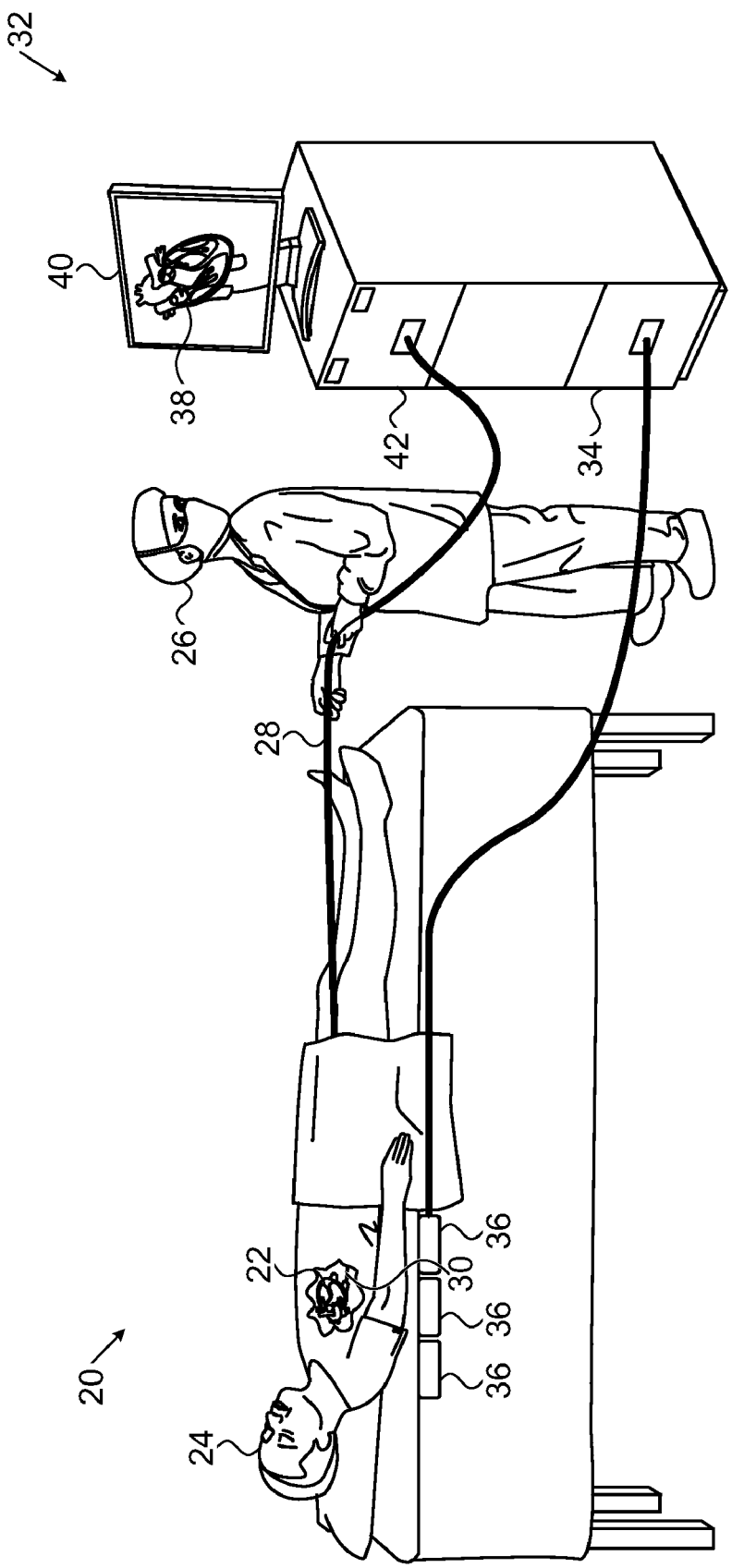
FIG. 1 is a schematic, pictorial illustration showing a system for mapping and treatment of CFAE, in accordance with an embodiment of the present invention.

The standard treatment for left-atrial fibrillation currently comprises catheter ablation around the pulmonary veins (PVI) and at other sites to eliminate residual drivers of AF. As noted above in the Background section, U.S. Patent Application Publication 2007/0197929 describes methods for acquiring a CFAE map, which shows locations of highly fractionated electrogram that are candidates for further ablation.

The CFAE phenomenon, however, is highly variable. Automatic algorithms for identifying CFAE, although reliable and reproducible, identify not only the truly active CFAE sites, representing critical fibrillatory substrate (collision, block, pivot points, slow conduction or ganglionated plexi), but also passive CFAE points, where the observed fractionation is the result of far-field phenomena, rather than local fibrillatory activity. At the passive CFAE points, the fractionated electrogram may result from the complex three-dimensional histological architecture of the atria, which causes summation and fractionation of signals from adjacent structures. Moreover, in chronic AF patients, structural remodeling of the heart tissue often causes asynchronous and discontinuous propagation of electrical potentials, with resulting passive fractionation of the bipolar electrogram signals. Only ablation of the active CFAE sites, where fractionation is localized, is actually of benefit the patient.

The distinction between active and passive CFAE is reinforced in a paper by Narayan et al., entitled "Classifying Fractionated Electrograms in Human Atrial Fibrillation Using Monophasic Action Potentials and Activation Mapping Evidence for localized Drivers, Rate Acceleration and Non-Local Signal Etiologies," *Heart Rhythm* (2010), which is incorporated herein by reference. The authors classify CFAEs in human AF into distinct functional types, which may be separated using monophasic action potentials (MAPs) and activation sequence. The MAPs indicate whether the CFAE is generated by local or non-local activity. The authors found that only a small minority of the CFAEs indicated localized rapid AF sites. The majority of CFAEs were found to reflect far-field signals, AF-acceleration or disorganization, corresponding to the "passive" types of CFAE points mentioned above, which are typically not critical to the fibrillatory process.

Ablating passive CFAE sites is not only unnecessary and time-consuming, but may lead to complications that compromise heart function. Therefore, embodiments of the present invention provide methods that may be used to distinguish between active and passive CFAE points during mapping. Such mapping is useful in limiting subsequent ablation to locations of actual therapeutic importance. Maps made in this manner enable the physician to perform ablation more selectively, at the truly active sites of CFAE, while avoiding unnecessary ablation and the resulting impairment of atrial function, collateral injury and atypical flutter.

The quality of measurement of CFAE depends on proper choice of recording parameters, such as recording time, contact area, unipolar vs. bipolar recording, and adequate filtering. Embodiments of the present invention are based on the specific assumption that the quality of contact between the measuring probe (typically a catheter with a suitable electrode) and the heart tissue is a determining factor in distinguishing between active and passive CFAE. Specifically, the correlation between MAPs and active CFAE leads to the conclusion that proper contact force and contact angle (close to the perpendicular) between the probe and the tissue are both important in identifying active CFAEs.

U.S. patent application Ser. No. 12/633,324, filed Dec. 8, 2009, whose disclosure is incorporated herein by reference, describes contact-gated mapping, based on measurements made by a catheter with a tip pressure sensor. The acquisition of electrophysiological mapping data is gated so that data points are acquired only when there is adequate contact between the probe and the tissue. The contact quality is verified by measuring the contact pressure exerted by the probe against the tissue. Map data points are acquired only when the contact quality is within a desired range. If the contact quality is out of range, the operator may be prompted to reposition the catheter.

Embodiments of the present invention, as described hereinbelow, take the principles of this mapping method a step further in order to control and improve the quality of mapping of fractionated electrograms. In the disclosed embodiments, a mapping processor receives electrical inputs measured by a probe at respective locations in a chamber of the heart of a subject. At each of the locations, the processor measures the contact quality between the probe and the heart tissue, typically using a suitable contact sensor in the probe. The processor then creates a map of complex fractionated electrograms in the heart chamber using the electrical inputs and the measured contact quality. The use of the contact quality measurement in processing the map points introduces objective criteria that are independent of operator expertise and mapping style.

Typically, the processor uses the contact quality to distinguish between points of active and passive fractionation. For this purpose, the processor may use the sensor in the probe to measure either the angle of contact between the probe and the tissue or the force of contact, or both. In one embodiment, map inputs are rejected if the angle of contact is outside a predetermined range of the perpendicular to the tissue, or the force is outside a predetermined force range.

System Description

FIG. 1 is a schematic, pictorial illustration of a system 20 for mapping and treatment of CFAE, in accordance with an embodiment of the present invention. System 20 may be based, for example, on the CARTO™ system, produced by Biosense Webster Inc. (Diamond Bar, Calif.). System 20 comprises a probe 28, such as a catheter, which is used by an operator 26, typically a cardiologist, in creating electrophysiological maps of a heart 22 of a patient 24. Operator 26 inserts probe 28 through the vascular system of patient 24 so that a distal end 30 of the probe enters a chamber of the heart. The operator advances and manipulates the probe in the body so that the distal tip of the probe engages endocardial tissue in the heart chamber at desired locations.

Probe 28 is connected at its proximal end to a console 32, which comprises a mapping processor 34. Processor 34 in this embodiment uses magnetic position sensing to determine position coordinates of distal end 30 inside heart 22. For this purpose, console 32 drives field generators 36 to generate magnetic fields within the body of patient 24. Typically, field generators 36 comprise coils, which are placed below the patient's torso at known positions and generate the magnetic fields in a predefined working volume that contains heart 22. A magnetic field sensor within distal end 30 of probe 28 (shown in FIGS. 3A-3C) outputs electrical signals in response to these magnetic fields. Mapping processor 34 processes these signals in order to determine the position coordinates of distal end 30, typically including both location and orientation coordinates. The method of position sensing described hereinabove is implemented in the above-mentioned CARTO™ system. Alternatively, system 20 may use any other suitable method of position sensing known in the art, such as ultrasonic or impedance-based sensing.

Mapping processor 34 typically comprises a general-purpose computer, with suitable front end and interface circuits for receiving signals from probe 28 and controlling the other components of system 20. Processor 34 may be programmed in software to carry out the functions that are described herein. The software may be downloaded to console 32 in electronic form, over a network, for example, or it may be provided on tangible media, such as optical, magnetic or electronic memory media. Alternatively, some or all of the functions of processor 34 may be carried out by dedicated or programmable digital hardware components.

Based on the signals received from probe 28 and other components of system 20, processor 34 drives a display 40 to present operator 26 with a map 38 of cardiac electrophysiological activity. In the present embodiment, processor 34 measures the quality of contact between distal end 30 and the tissue in heart 22, as described in detail hereinbelow, and uses the contact quality in selecting and controlling the data from the probe that go into map 38. Specifically, the processor may map CFAEs, while including in the map only those points that meet certain contact quality criteria and rejecting points that fall outside these criteria.

Display 40 may also provide visual feedback regarding the position of distal end 30 in the patient's body and status information and guidance regarding the procedure that is in progress. For example, display 40 may provide visual feedback to operator 26 regarding the contact quality between distal end 30 and the endocardial tissue, such as the contact force and angle. If the contact parameters are outside a specified range, processor 34 may prompt operator 26 to reposition probe 28.

Alternatively or additionally, system 20 may comprise an automated robotic mechanism (not shown) for maneuvering and operating probe 28 within the body of patient 24. Such mechanisms are typically capable of controlling both the longitudinal motion (advance/retract) of the probe and transverse motion (deflection/steering) of distal end 30 of the probe. In such embodiments, processor 34 generates a control input for controlling the motion of probe 28 based on the signals provided by the probe, which are indicative of both the position of distal end 30 and of the contact parameters.

Console 32 also comprises an energy generator 42, which provides energy to probe 28 for ablating pathological sites in heart 22. For example, energy generator 42 may provide radio frequency (RF) energy to an electrode (shown in the figures that follow) at the distal tip of probe 28 for performing RF ablation. The ablation may be guided by map 38 to sites of active CFAE, as described in detail hereinbelow.

Figure 2:
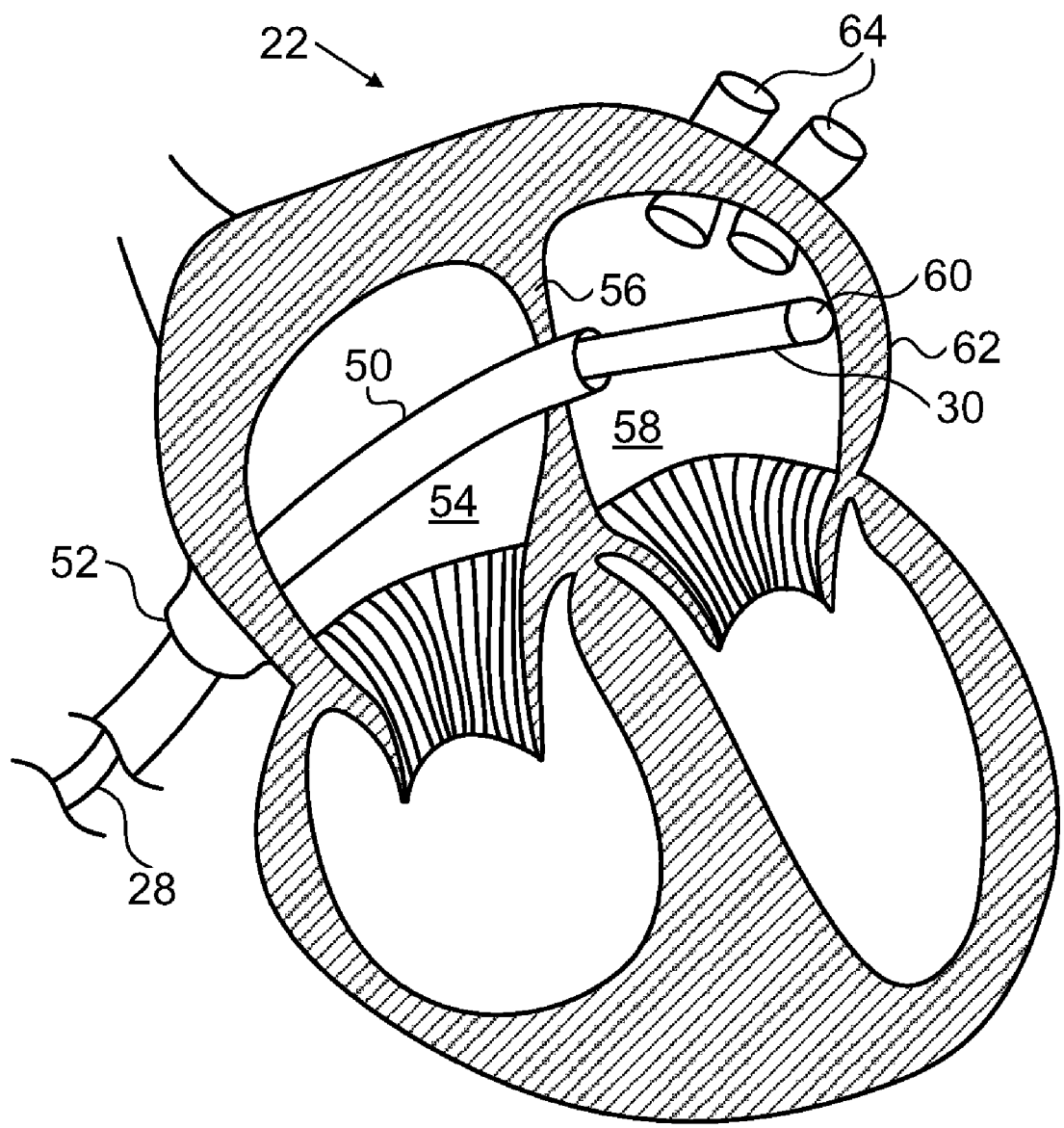
FIG. 2 is a schematic, sectional illustration of a heart showing the operation of a mapping probe therein, in accordance with an embodiment of the present invention.

FIG. 2 is a schematic, sectional view of heart 22, showing the operation of probe 28 therein, in accordance with an embodiment of the present invention. This figure illustrates a typical mapping procedure in a left atrium 58 of heart 22, but the principles of this embodiment may similarly be implemented in other heart chambers.

To map left atrium 58, a sheath 50 is typically inserted via the vascular system, such as through an inferior vena cava 52, into a right atrium 54 of the heart, and then penetrates into the left atrium by puncturing an interatrial septum 56. Distal end 30 of probe 28 is inserted through sheath 50 into the left atrium. An electrode 60 at the distal tip of the catheter is brought into contact with endocardial tissue 62 at multiple locations in left atrium 58. Electrode 60 is typically made of a metallic material, such as a platinum/iridium alloy or another suitable conductor.

At each location in atrium 58 where catheter 28 contacts tissue 62, processor 34 receives electrical signals from electrode 60 (and possibly from other electrodes [not shown] along the length of distal end 30). The processor also receives position signals indicating the location and, optionally, the orientation of distal end 30, as well as signals that are indicative of the quality of contact between the probe tip and the tissue. The position signals may be the result of magnetic position sensing, as described above, or of any other suitable method of position sensing. The contact quality signals may be derived in any suitable manner known in the art, such as those described in the above-mentioned patent applications, and are typically indicative at least of the force of contact between distal end 30 and tissue 62, as well as the angle of contact.

Processor 34 uses the electrical signals, position signals, and contact quality signals in creating a map of CFAE in left atrium 58, as described further hereinbelow. The map indicates in particular active CFAE sites, i.e., sites of local CFAE, as explained above. Operator 26 may then treat arrhythmias in the left atrium by applying RF energy to electrode 60 in order to ablate the active CFAE sites, typically in addition to ablating around the ostia of pulmonary veins 64.

Figure 3A:
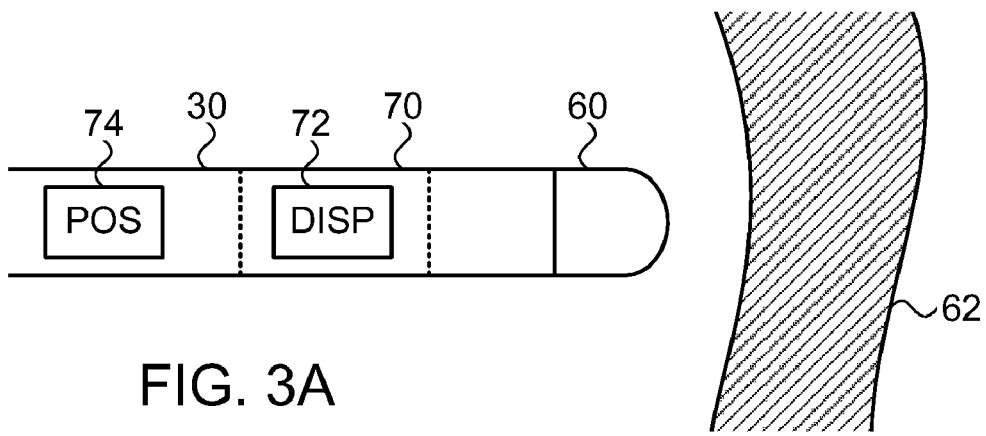
FIGS. 3A, 3B and 3C are schematic side views of a probe inside a chamber of the heart in the course of mapping CFAE, in accordance with an embodiment of the present invention.
Figure 3B:
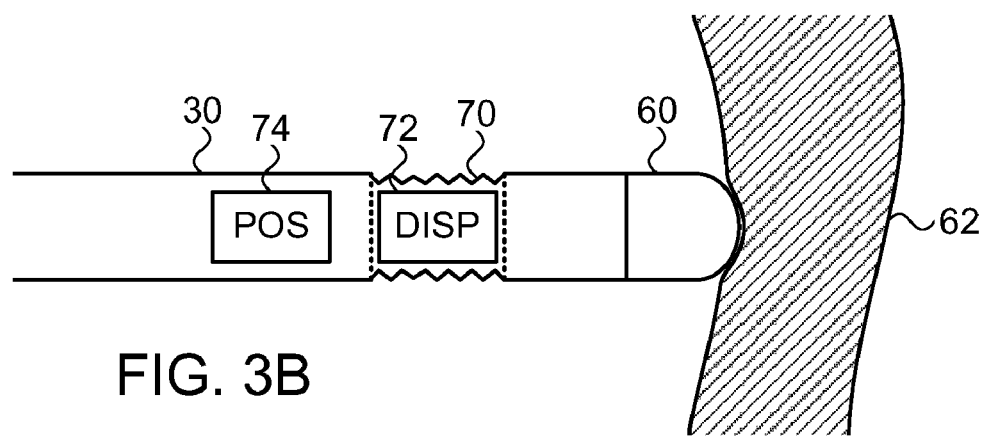
Figure 3C:
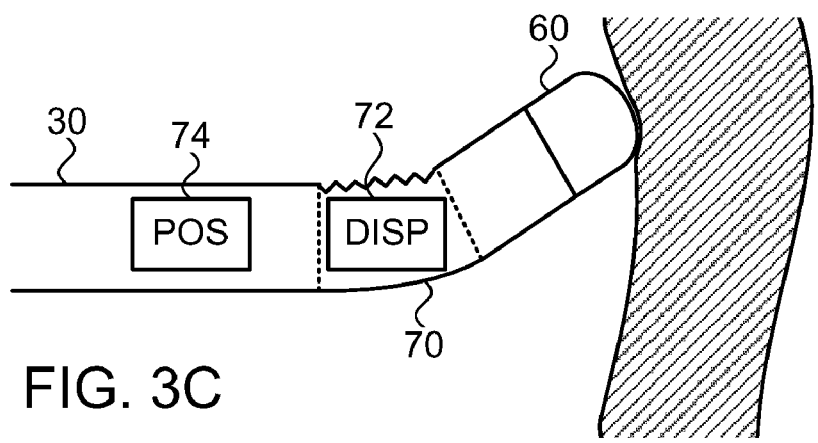

FIGS. 3A, 3B and 3C are schematic side views of distal end 30 of probe 28, in accordance with an embodiment of the present invention. These figures show functional elements of distal end 30 that are used in creating a map of cardiac electrical activity. In FIG. 3A, distal end 30 is shown approaching endocardial tissue 62, but electrode 60 at the distal tip of the probe is not yet in contact with the tissue. FIGS. 3B and 3C show different contact configurations.

A position sensor 74 in distal end 30 generates a signal to console 32 that is indicative of the position coordinates of distal end 30. For magnetic position sensing, the position sensor may comprise one or more miniature coils, and typically comprises multiple coils oriented along different axes. Alternatively, position sensor 74 may comprise either another type of magnetic sensor, or an electrode which serves as a position transducer, or position transducers of other types, such as an ultrasonic position sensor. Although FIGS. 3A-3C show a probe with a single position sensor, other embodiments may use probes with multiple position sensors. Further alternatively or additionally, distal end 30 may comprise a magnetic field generator, whose field is received by sensing coils outside the body in order to find the position of the probe. As yet another alternative, the position of distal end 30 may be found by fluoroscopy or other methods of imaging that are known in the art.

A displacement sensor 72 in distal end 30 senses contact between the distal tip of the probe and endocardial tissue 62. Sensor 72 generates signals to processor 34 that are indicative of the deformation of a resilient member 70 in distal end 30. The amount and direction of this deformation are indicative of both the force exerted by the distal tip of the probe against the tissue and the angle of contact. Further details of this sort of probe and sensing arrangement are described in the above-mentioned U.S. Patent Application Publications 2009/

0093806 and 2009/0138007. Alternatively, distal end 30 may comprise any other suitable type of contact sensor.

In FIG. 3B, distal end 30 engages tissue 62 head-on, with adequate contact force (typically 20-30 grams) to ensure good electrical contact between electrode 60 and the tissue. As the result of the tissue contact, resilient member 70 is compressed, and the signal from sensor 72 to processor 34 is indicative of this head-on compression. In this tissue contact configuration, the electrical signals sensed by electrode 60 are generally dominated by local tissue activity. If a CFAE is detected in this configuration, it is likely that the tissue location contacted by the electrode is an active CFAE site. By contrast, in the configuration shown in FIG. 3A, it is likely that any CFAE activity sensed by electrode 60 is influenced heavily by the far-field, rather than of local origin.

In FIG. 3C, distal end 30 engages tissue 62 obliquely, with the result that member 70 bends. In this contact configuration, the electrical signals sensed by electrode 60 may be more susceptible to far-field influences, even when there is adequate contact force between the distal end of the probe and the tissue. Therefore, if a CFAE is detected in this configuration, there is a higher likelihood that the tissue location in question is a passive, rather than active, CFAE site. The signals output by sensor 72 to processor 34 are indicative of the bend angle, as well as the contact force, and the processor may thus take the angle of contact into account in assessing whether to classify the tissue location as an active or passive CFAE site.

Figure 4:
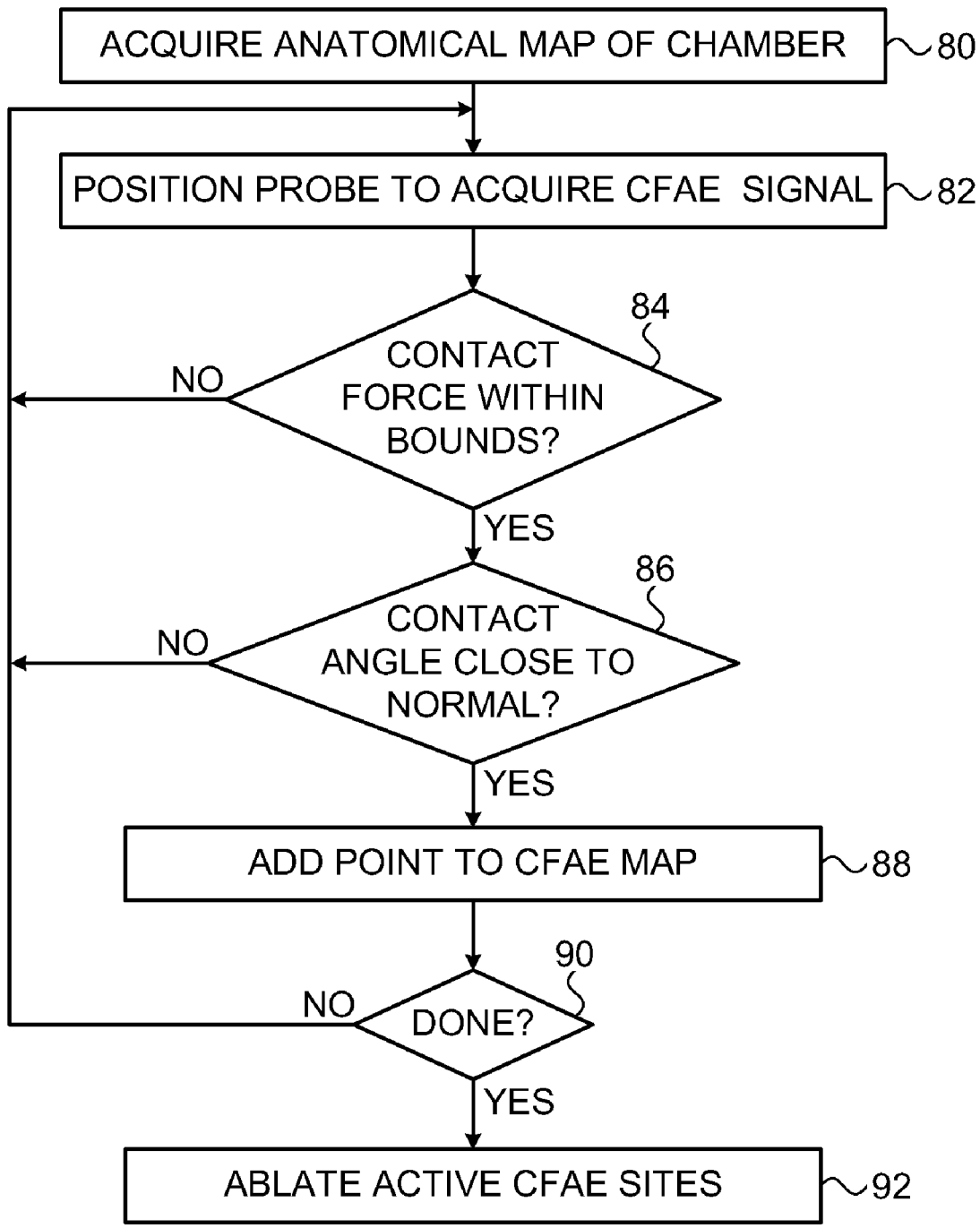
FIG. 4 is a flow chart that schematically illustrates a method for mapping and treatment of CFAE, in accordance with an embodiment of the present invention.

FIG. 4 is a flow chart that schematically illustrates a method for mapping and treatment of CFAE, in accordance with an embodiment of the present invention. For convenience and simplicity, the method is set forth hereinbelow with reference to probe 28 and to the other components of system 20, as described above. Alternatively, the principles of this method may be applied using any suitable sort of electrophysiological mapping system with the appropriate sensing and signal processing capabilities. Furthermore, although the method as described below involves the interaction of operator 26 in manipulating probe 28, at least some of the steps of the method may alternatively be carried out by system 20 automatically under robotic control, as noted above.

As a first step in the method, it is useful to acquire an anatomical map of the heart chamber of interest (left atrium 58 in this example), at an anatomical mapping step 80. The map may be acquired by any suitable method known in the art. For example, processor 34 may collect location coordinates from probe 28 as operator 26 moves the probe around within atrium 58, and then may process this collection of coordinates to find its bounding surface, corresponding to the inner wall of the atrium. Additionally or alternatively, processor 34 may register the location of probe 28 with a pre-acquired ultrasound or CT image, which has been segmented to show atrium 58. Further alternatively, the anatomical map may be acquired concurrently with CFAE mapping.

To acquire CFAE map points, operator 26 positions distal end 30 so that electrode 60 engages tissue 62, at a signal acquisition step 82. Processor 34 receives and analyzes the signals from electrode 60 in order to detect fractionation and thus identify points of CFAE. Any suitable method of signal analysis may be used for this purpose, such as the methods described in the above-mentioned U.S. Patent Application Publication 2007/0197929.

Before adding a CFAE point to the map, however, processor 34 checks the contact quality, based on the signals output by sensor 72. Typically, the processor checks whether the force of contact is within acceptable bounds, at a force checking step 84. For example, the processor may verify that the force is between 5 and 40 grams or, more stringently, between 20 and 30 grams. Additionally or alternatively, the processor checks whether the angle of contact is normal or nearly so, i.e., the processor verifies that distal end 30 of probe 28 is within a predetermined angular range of the perpendicular to tissue 60. Since it is difficult to make an accurate measurement of the local angle of contact between the probe and the tissue directly, the processor may infer the contact angle from the bend angle indicated by sensor 72. For example, the processor may conclude that the contact angle is within an acceptable range of the normal if the bend angle indicated by sensor 72 is less than 15°.

If the above contact quality criteria are satisfied at a point of CFAE, processor 34 classifies the CFAE point as an active CFAE site and adds it to the CFAE map, at an active mapping step 88. Otherwise, the processor may discard the CFAE point and may optionally prompt operator 26 to correct the contact force and/or angle and then attempt to reacquire the point. Alternatively, the processor may mark the CFAE points according to their respective contact quality and may then color or otherwise mark the points on the CFAE map accordingly. Further additionally or alternatively, processor 34 may simultaneously create two separate "raw" maps: one of CFAE and the other of contact quality, and may then generate a map of active CFAE sites as the intersection of the raw maps.

System 20, under the control of operator 26, repeats steps 82-88 until a sufficiently dense and complete CFAE map has been created, at a mapping completion step 90. The operator may then proceed to ablate the active CFAE sites that are marked on the map, at an ablation step 92. This ablation is typically (although not necessarily) carried out, as noted above, in conjunction with PVI ablation. Alternatively, the map of active CFAE may be used for diagnosis and follow-up, without performing ablation immediately after mapping.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for mapping complex fractionated electrograms in a chamber of a heart of a subject using a probe, comprising:
    receiving electrical inputs measured by the probe at respective locations in the chamber of the heart of the subject;
    processing the electrical inputs to identify complex fractionated electrograms;
    measuring, at each of the respective locations, a respective contact quality between the probe and a tissue in the chamber; and
    creating a map of the complex fractionated electrograms in the chamber using the electrical inputs and the measured contact quality to distinguish between active and passive complex fractionated electrograms.

2. The method according to claim 1, wherein measuring the respective contact quality comprises assessing an angle of contact between the probe and the tissue.

3. The method according to claim 2, wherein measuring the respective contact quality further comprises measuring a force of contact between the probe and the tissue.

4. The method according to claim 2, wherein creating the map comprises rejecting the inputs for which the angle of contact is outside a predetermined angular range of a perpendicular to the tissue.

5. The method according to claim 2, wherein assessing the angle of contact comprises measuring a bend angle of a distal end of the probe.

6. The method according to claim 1, wherein measuring the respective contact quality comprises measuring a force of contact between the probe and the tissue.

7. The method according to claim 6, wherein creating the map comprises rejecting the inputs for which the force of contact is outside a predetermined range.

8. The method according to claim 1, wherein the chamber is a left atrium of the heart.

9. The method according to claim 8, and comprising ablating sites in the left atrium at which the complex fractionated electrograms were detected while the contact quality satisfied a predetermined contact criterion.

10. The method according to claim 9, wherein the predetermined contact criterion requires that a force of contact and an angle of contact between the probe and the tissue be within respective predetermined ranges.

11. The method according to claim 1, wherein creating the map comprises selectively mapping active sites of fractionated electrical activity responsively to the measured contact quality.

12. Mapping apparatus, comprising:
 a probe, which is configured to sense electrical activity in a chamber of a heart of a subject; and
 a processor, which is configured to receive and process electrical inputs from the probe at multiple locations in the chamber so as to identify complex fractionated electrograms, to measure, at each of the locations, a respective contact quality between the probe and a tissue in the chamber, and to create a map of the complex fractionated electrograms in the chamber using the electrical inputs and the measured contact quality to distinguish between active and passive complex fractionated electrograms.

13. The apparatus according to claim 12, wherein the processor is configured to measure the contact quality by assessing an angle of contact between the probe and the tissue.

14. The apparatus according to claim 13, wherein the contact quality measured by the processor is further based on a measurement of a force of contact between the probe and the tissue.

15. The apparatus according to claim 13, wherein the processor is configured to reject the inputs for which the angle of contact is outside a predetermined angular range of a perpendicular to the tissue from inclusion in the map.

16. The apparatus according to claim 13, wherein the processor is configured to assess the angle of contact by measuring a bend angle of a distal end of the probe.

17. The apparatus according to claim 12, wherein the processor is configured to measure the contact quality based on a force of contact between the probe and the tissue.

18. The apparatus according to claim 17, wherein the processor is configured to reject the inputs for which the force of contact is outside a predetermined range.

19. The apparatus according to claim 12, wherein the chamber is a left atrium of the heart.

20. The apparatus according to claim 19, and comprising an energy generator, which is operable to apply energy to the probe so as to ablate sites in the left atrium at which the complex fractionated electrograms were detected while the contact quality satisfied a predetermined contact criterion.

21. The apparatus according to claim 20, wherein the predetermined contact criterion requires that a force of contact and an angle of contact between the probe and the tissue be within respective predetermined ranges.

22. The apparatus according to claim 12, wherein the map selectively includes active sites of fractionated electrical activity, which are identified responsively to the measured contact quality.

23. A computer software product, comprising a non-transitory computer-readable medium in which program instructions are stored, which instructions, when read by a processor, cause the processor to receive electrical inputs from a probe in response to electrical activity at multiple locations in a chamber of a heart of a subject, to process the electrical inputs so as to identify complex fractionated electrograms, to measure, at each of the locations, a respective contact quality between the probe and a tissue in the chamber, and to create a map of the complex fractionated electrograms in the chamber using the electrical inputs and the measured contact quality to distinguish between active and passive complex fractionated electrograms.

* * * * *